United States Patent [19]

Chung

[11] 4,105,680

[45] Aug. 8, 1978

[54] PROCESS FOR THE PREPARATION OF 1-AMINOANTHRAQUINONES

[75] Inventor: Rack H. Chung, Clifton Park, N.Y.

[73] Assignee: GAF Corporation, New York, N.Y.

[21] Appl. No.: 834,994

[22] Filed: Sep. 20, 1977

[51] Int. Cl.$^2$ .................. C09B 1/22; C07C 49/68; C07C 25/00

[52] U.S. Cl. .................. 260/378; 260/522; 260/376

[58] Field of Search .............. 260/369, 384, 376, 522, 260/378

[56] References Cited

U.S. PATENT DOCUMENTS

| | | | |
|---|---|---|---|
| 1,551,373 | 8/1925 | Daudt | 260/522 |
| 1,966,067 | 7/1934 | Jaeger | 260/522 |
| 2,439,237 | 4/1948 | Cass | 260/522 |
| 3,230,259 | 1/1966 | Levy | 260/689 |
| 3,978,096 | 8/1976 | Eilingsfeld et al. | 260/384 |

FOREIGN PATENT DOCUMENTS 197,050  9/1967  U.S.S.R. .................. 260/376

*Primary Examiner*—Allen B. Curtis
*Assistant Examiner*—Raymond K. Covington
*Attorney, Agent, or Firm*—Walter C. Kehm; Marilyn J. Maue

[57] ABSTRACT

A selective process for the preparation of 1-aminoanthraquinones by decarboxylation of the corresponding 1-aminoanthraquinone-2-carboxylic acid in an alkaline solution with an alkali metal hydrosulfite.

9 Claims, No Drawings

PROCESS FOR THE PREPARATION OF 1-AMINOANTHRAQUINONES

The present invention provides a simplified and efficient process for selectively producing 1-aminoanthraquinones in a substantially pure state and in high yield.

The 1-aminoanthraquinone is an important intermediate in the manufacture of a wide variety of dyestuffs, pharmaceuticals, thickening agents, etc., being used either as such or after conversion to a corresponding derivative. Specifically, 1-aminoanthraquinone is used in the manufacture of bromamine acid and 1-amino-2-bromo4-hydroxyanthraquinone from which Genacron Cerise N and Genacron Cerise NSL and other valuable dyestuffs are produced.

Typical reactions for the 1-aminoanthraquinone isomer are treatment with concentrated oleum or chlorosulfonic acid to form the 1-amino-2-sulfonic acid derivative followed by treatment with bromine to form bromamine (1-amino-4-bromoanthraquinone-2-sulfonic acid), or the 1-amino-anthraquinone compound can be dibrominated to form 2,4-dibromo-1-aminoanthraquinone, which, in turn can be hydrolyzed with concentrated sulfuric and boric acids to provide 1-amino-2-bromo-4-hydroxyanthraquinone. The 1-aminoanthraquinone can also be treated with chloroform to give the isocyanide derivative and reaction with nitrous acid gives the corresponding diazonium salt which, in turn, is hydrolyzed to the hydroxy derivative.

In the past, 1-aminoanthraquinone has been prepared by treatment of anthraquinone with oleum in the presence of mercury to produce anthraquinone-1-sulfonic acid which, in turn, is reacted with ammonia in the presence of arsenic. Since the present process does not require mercury or arsenic, it avoids serious pollution problems associated with their use and disposal.

Further disadvantages of prior processes using mercury and arsenic appear to be due to the fact that traces of these elements can be found in the final product, which are prohibitive in the preparation of pharmaceuticals.

Accordingly, it is an object of the present invention to provide a commercially feasible and economical process for the selective production of 1-aminoanthraquinone and substituted derivatives thereof.

It is another object of the present invention to provide a process for the production of 1-aminoanthraquinone in high yield and in a substantially pure state, e.g. above about 95%.

These and other objects of the present invention will become apparent from the following description and disclosure.

In accordance with the present invention, a 1-aminoanthraquinone-2-carboxylic acid having the formula:

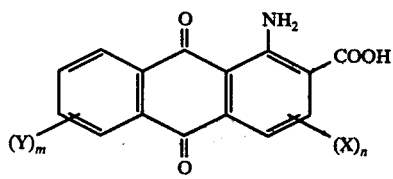

wherein X is hydroxy, alkoxy of from 1 to 4 carbon atoms, halo, amino or —$SO_3H$; Y is hydroxy, alkoxy of from 1 to 4 atoms, halo, amino or —$SO_3H$; and $m$ and $n$ independently represent a value of from 0 to 2, is dissolved in an alkali metal hydroxide solution and decarboxylated in the presence of an alkali metal hydrosulfite, at a temperature of from about 50° C. to about 150° C. under from about 5 to about 100 psig, preferably at a temperature of from about 80° C. to about 110° C. under atmospheric pressure. The acid is preferably dissolved directly in the hydroxide solution; although, if desired, it may be predissolved in a solvent and then added to the hydroxide solution in a reaction zone.

Suitable solvents for presolubilizing the acid include dialkyl ethers of 2-6 carbon atoms or cellosolve, that is hydroxy ethyl ethyl ether, N-alkylpyrrolidones, such as N-methylpyrrolidone; di-lower alkyl formamides, such as dimethyl formamide; etc.

The alkaline solution of 1-aminoanthraquinone-2-carboxylic acid is preferably prepared by dissolving the acid in an aqueous solution of an alkali metal hydroxide, preferably KOH or NaOH, of between about 0.1 molar and about 1 molar concentration, preferably between about 0.18 molar and about 0.5 molar concentration. The moles of alkali metal hydroxide per mole of acid may vary between about 2 and about 10, and is preferably between about 4 and about 8. To this solution is added from about 0.75 mole to about 3 moles, more desirably between about 1.5 moles and about 2.25 moles, of the alkali metal hydrosulfite per mole of 1-aminoanthraquinone-2-carboxylic acid. The mixture is then reacted at elevated temperature, preferably by refluxing for a period of from about 0.5 to about 8 hours, more desirably from about 1 to about 4 hours, during which time carbon dioxide gas is generated. The carbon dioxide by-product can be vented to the atmosphere or the reaction can be conducted in a closed system wherein the generation of carbon dioxide gradually increases the pressure and the reaction is run under autogenous conditions. If desired, the reaction can be run under a blanket of nitrogen gas; although such operation under nitrogen is not necessary to achieve the benefits of the present invention. A pH of between about 8 and about 10 is maintained during reaction.

After the reaction is completed as noted by constant pressure or cessation of carbon dioxide generation, the reaction product which is formed as a precipitate, is cooled, filtered, water washed and dried to selectively produce 1-aminoanthraquinone. The product may be recrystallized from glacial acetic acid if desired, but is directly obtained in sufficient purity for immediate use without further purification.

By the process of the present invention, the 1-aminoanthraquinone product is recovered in at least 70% yield and in a substantially pure state. This product is suitable for further reaction without additional purification; thus, the 1-aminoanthraquinone obtained in this manner can be directly used as a valuable coupling agent or converted to other dyestuff intermediates, such as, 1-amino-4-bromoanthraquinone-2-sulfonic acid or 1-amino-2-bromo-4-hydroxyanthraquinone.

The 1-aminoanthraquinone-2-carboxylic acid starting materials of the present process are prepared by the general process of the following equation:

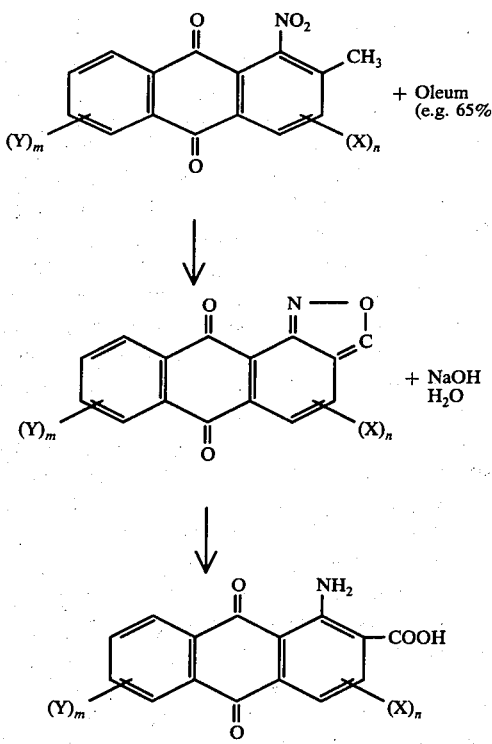

wherein X, Y, m and n are as defined above. This reaction, after the addition of oleum, is effected at a temperature between about −5° C. and about 10° C. under atmospheric pressure.

Having generally described the present invention, reference is now had to the accompanying examples which illustrate preferred embodiments, but which are not to be construed as limiting to the scope of the present invention as set forth in the foregoing disclosure and in the appended claims. All amounts and proportions recited in the following examples are by weight unless otherwise indicated. It is also to be understood that any of the substituted 1-aminoanthraquinone-2-carboxylic acids can replace 1-aminoanthraquinone-2-carboxylic acid in the following examples to provide the corresponding, decarboxylated product.

EXAMPLE 1

1-Nitro-2-methylanthraquinone (30 g 0.11 mole) was added to 125 ml. of 65% oleum in portions sufficient to maintain the temperature below 5° C. The temperature at 5° C. is assisted by means of an ice-salt bath. After the addition was complete the mixture was stirred for 15 minutes at the same temperature. The reaction mixture was then poured slowly over ice. The dark brownish-yellow solid which formed was collected by filtration and washed with water. The wet cake was heated with 1130 ml. of 10% sodium hydroxide solution for 1 hour at 100° C. After being cooled to room temperature, the mixture was acidified with 6N hydrochloric acid. The solid 1-aminoanthraquinone-2-carboxylic acid which precipitated was collected by filtration and washed with water.

The crude wet cake of 1-aminoanthraquinone-2-carboxylic acid was dissolved in 1500 ml. of water and 50 ml. of 10 M sodium hydroxide solution. The mixture was heated on a steam bath, and 35 g (0.2 mole) sodium hydrosulfite was added. Heating was continued until a red solid formed. The reaction mixture was then cooled to room temperature, and the red solid was collected by filtration and washed with water to give 18.5g (74% yield) of 1-aminoanthraquinone. The Thin Layer Chromatogram of the crude product showed the presence of less than 5% of impurity.

EXAMPLE 2

1-Aminoanthraquinone-2-carboxylic acid was prepared in the manner described in Example 1 from 30 g (0.11 mole) of 1-nitro-2-methylanthraquinone.

The wet cake of 1-aminoanthraquinone-2-carboxylic acid was dissolved in 2000 ml. of water and 50 ml. of 10 M sodium hydroxide solution. The mixture was heated on a steam bath to 90°–100° C. and 40 g (0.23 mole) sodium hydrosulfite was added. Heating was continued with stirring for 2 hours, after which the mixture was cooled to room temperature. The resulting red solid was collected by filtration and washed with water until the filtrate was neutral. The solid was dried at 80° C. to give 19.5 g (78% yield) of 1-aminoanthraquinone. The Thin Layer Chromatogram of the crude product showed the presence of less than 5% of impurity.

EXAMPLE 3

1-Amino-4-hydroxyanthraquinone-2-carboxylic acid (31.1 grams, 0.11 mole) was dissolved in 2000 ml. of water and 50 ml. of 10 M sodium hydroxide solution. The mixture was heated on a steam bath to 90°–100° C., and 40 g (0.23 mole) sodium hydro ulfite was added. Heating was continued with stirring for 2 hours, after which the mixture was cooled to room temperature. The resulting solid was collected by filtration and washed with water until the filtrate was neutral. The solid was dried at 80° C. to give 26.2 g (75% yield) of 1-amino-4-hydroxyanthraquinone. The Thin Layer Chromatogram of the crude product showed the presence of a small amount of impurity.

EXAMPLE 4

1-Amino-4-bromoanthraquinone-2-carboxylic acid (38 grams, 0.11 mole) was dissolved in 200 ml. of water and 50 ml. of 10 M sodium hydroxide solution. The mixture was heated on a steam bath to 90°–100° C., and 40 g (b 0.23 mole) sodium hydrosulfite was added. Heating was continued with stirring for 2 hours, after which the mixture was cooled to room temperature. The resuting solid was collected by filtration and washed with water until the filtrate was neutral. The solid was dried at 80° C. to give 24.9 g (75% yield) of 1-amino-4-bromoanthraquinone. The Thin Layer Chromatogram of the crude product showed the presence of a small amount of impurity.

What is claimed is:

1. A process for selectively producing a 1-aminoanthraquinone which comprises:
    (a) forming an alkali metal hydroxide solution of a 1-aminoanthraquinone-2-carboxylic acid having the formula:

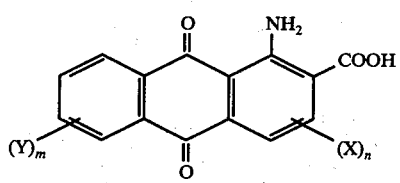

wherein X is hydroxy, alkoxy of from 1 to 4 carbon atoms, halo, amino or —SO₃H; Y is hydroxy, alkoxy of from 1 to 4 carbon atoms, halo, amino or —SO₃H; and m and n independently represent a value of from 0 to 2;

(b) contacting the resulting alkali metal hydroxide solution from (a) with between about 0.75 mole and about 3 moles of an alkali metal hydrosulfite, per mole of 1-aminoanthraquinone-2-carboxylic acid to effect decarboxylation at an elevated temperature; and (c) recovering the corresponding product of the process having the formula:

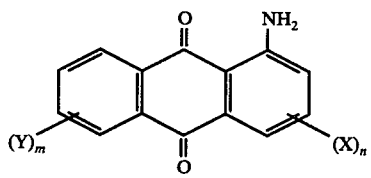

wherein the substituents X and Y and subscripts $m$ and $n$ are the same as defined above.

2. The process of claim 1 wherein the alkali metal hydroxide solution is an aqueous 0.1 to 1 molar solution.

3. The process of claim 2 wherein between about 2 and about 10 moles of the alkali metal hydroxide per mole of the 1-aminoanthraquinone-2-carboxylic acid is employed.

4. The process of claim 1 wherein the decarboxylation is effected at between about 50° C. and about 150° C. under from about 5 psig to about 100 psig.

5. The process of claim 4 wherein the decarboxylation is effected at between about 80° C. and about 110° C. under atmospheric pressure.

6. The process of claim 1 wherein the reaction is conducted over a period of from about 0.25 hour to about 5 hours.

7. The process of claim 6 wherein the reaction is conducted over a period of from about 1 hour to about 4 hours.

8. The process of claim 1 wherein the alkaline solution is formed by combining the 1-aminoanthraquinone-2-carboxylic acid with an aqueous solution of an alkali metal hydroxide having between about 0.18 and 0.5 molar base concentration and mixing between about 4 and about 8 moles of alkali metal hydroxide per mole of said acid to provide the solution of step (a).

9. The process of claim 1 wherein the 1-aminoanthraquinone-2-carboxylic acid is unsubstituted as when $m$ and $n$ are 0.

* * * * *